US005785716A

United States Patent [19]
Bayron et al.

[11] Patent Number: 5,785,716
[45] Date of Patent: Jul. 28, 1998

[54] TEMPERATURE CONTROL PAD FOR USE DURING MEDICAL AND SURGICAL PROCEDURES

[76] Inventors: Harry Bayron, 7439 Pioneer Rd., West Palm Beach, Fla. 33413; Neil Winthrop, 12A Amherst Ct., Royal Palm Beach, Fla. 33411

[21] Appl. No.: 647,226

[22] Filed: May 9, 1996

[51] Int. Cl.$^6$ ........................................... A61F 7/00
[52] U.S. Cl. .................... 607/108; 607/112; 607/114; 126/204; 128/854
[58] Field of Search ............ 607/96, 104, 107–112, 607/114; 128/849–855; 165/46; 126/204; 62/4

[56] References Cited

U.S. PATENT DOCUMENTS

| | | | |
|---|---|---|---|
| 4,471,769 | 9/1984 | Lockhart | 128/849 |
| 5,184,612 | 2/1993 | Augustine | 607/108 X |
| 5,383,918 | 1/1995 | Panetta | 607/108 X |
| 5,443,488 | 8/1995 | Namenye | 607/114 X |

Primary Examiner—John P. Lacyk
Assistant Examiner—Ryan Carter
Attorney, Agent, or Firm—McHale & Slavin

[57] ABSTRACT

A heating or cooling pad device, particularly for use in surgical operations and medical procedures, which has a human shaped pad for receiving a lying body. The heating or cooling pad can be formed from a chemical reaction pack to generate heat or cold. Alternatively, the pad may consist of an inflatable structure which conducts thermally controlled pressurized fluid from an inlet port through a series of interacting channels to an outlet port. The pad might also have a concave curvature on its surface to thereby cradle a patient when inflated. A stiffener might be adhered to the lower surface of the pad. The pad includes a series of hook and pile attachment strips for selectively attaching modular sections of insulated material which can then be used to wrap around and secure the patient lying on the pad. A single piece section of insulated material might also be used underneath the pad, with the section having flaps which extend around to secure and insulate the patient. Additionally, separate torso and headpiece sections of insulated material can be used to facilitate selective access to various parts of the patient, and yet optimize thermal energy conversation in and around the patient.

20 Claims, 4 Drawing Sheets

TEMPERATURE CONTROL PAD FOR USE DURING MEDICAL AND SURGICAL PROCEDURES

FIELD OF INVENTION

This invention relates to a heating and/or cooling pad and in particular a human body shaped pad placed beneath a patient allowing heat or cold to radiate upwards. The pad includes thermally insulated straps which can be used to further insulate and selectively secure various parts of the patient's body to the pad.

BACKGROUND OF THE INVENTION

It is important to maintain a patient's body temperature at a precise level during various neonatal, adult, and pediatric medical procedures. Such procedures include surgery, x-rays, invasive and non-invasive testing, patient transport, trauma for use in ambulance, childbirth in ambulance, and thermal regulation. Such importance is particularly true during surgical operations. During surgery, the body temperature naturally tends to drop as heat is readily lost from exposed body parts. Heat loss places a surgery patient in a vulnerable condition wherein the patient may succumb to hypothermia and even death. This heat loss problem and the resulting detrimental effects are even more pronounced in infants. Other specialized surgeries might require the application of cold.

Accordingly, operating room techniques attempt to assure that a patient's temperature is maintained during a medical procedure. Such attempts include raising the overall temperature of the room, and/or bringing warming lights into close proximity with the patient. Unfortunately, such attempts fail to properly warm the patient and create an uncomfortable environment for the medical personnel. Surgeons have even been known to wrap the top of their heads in aluminum foil to try and reflect away some of the heat from the warming lamps. In general, such conditions are not productive due to the discomfort rendered to the medical personnel. Moreover, such conditions might cause a surgeon to be distracted during a medical procedure, possibly placing the patient at an additional risk. Extreme cooling of the operating room would present similar problems.

A variety of devices have been disclosed for controlling or enhancing a person's body temperature. U.S. Pat. Nos. 2,648,325; 4,856,294; and 5,484,448 disclose vest-like garments which can be worn to heat or cool body temperature. Such devices utilize heating and/or cooling packs, but are not readily applicable to medical or surgical procedures.

U.S. Pat. No. 3,738,367 discloses a garment which conforms to different body shapes. The fabric contains a series of embedded tubes for conveying heating or cooling fluids as circulated by a hyperthermia machine. Zippers allow access to some parts of the body while the garment is being worn. U.S. Pat. No. 5,269,369 similarly discloses a temperature regulation system which uses fabric embedded tubes to distribute energy to various portions of the body. The regulation system may be used for a garment, a blanket, and/or a pad and runs in various patterns as needed for the particular application. U.S. Pat. No. 5,383,918 discloses a compartmentalized heat conserving/cooling body suit. The suit encloses the entire body and requires circulated air for temperature regulation. A blanket is disclosed in U.S. Pat. No. 5,405,370 which similarly uses heated or cooled air for temperature regulation.

U.S. Pat. No. 5,184,613 discloses a thermal pack with opposing identical sections which wrap around the limb of an individual, particularly the heel of an infant, and is secured in position with VELCRO strips. The thermal pack consists of a flexible fluid pouch with hour glass shaped sections which provide a quilt-like appearance. As noted in this patent, the use of thermal packs to generate heat is well known according to various prior art techniques. The typical thermal pack employs a sealed rectangular package containing selected chemical ingredients which, when finally intermixed together, provide a refrigerated or a heated pack.

Numerous examples of such thermal packs exist, such as those disclosed in U.S. Pat. Nos. 4,057,047; 4,856,651; and 4,580,547. As such, these patents disclose heating pads where one packet of chemicals is suspended within another and the weaker inner packet is broken to provide mixing of the fluids, thereby causing a chemical reaction. Additionally, these patents disclose reactions which occur as a result of a trigger being activated inside the pack. Such triggers include a thin, bendable, metallic strip which can be flexed to initiate exothermic crystallization of a salt which is in solution.

While the above mentioned patents and disclosures show assorted attempts to address the heating and/or cooling of body parts, the varied problems encountered during a surgical procedure are not addressed. What is needed in the field is a specially shaped pad which is capable of generating and/or dispensing heat or cold in an even manner. This could be accomplished through a chemical reaction pack, or through circulated fluids. The pad should be placed under the patient and heat or cold will be radiated upwards to maintain the patient's body temperature during surgery, transport, or otherwise. Accordingly, a human shaped pad would ideally be suited for such applications as it would minimize the space required and would localize heat or cold application.

Additionally, insulated material should be provided which can be modularly attached to the pad in sections and which can wrap around various body parts and be releasably secured over the patient as needed. Such insulated material must prevent localized heat or cold loss and trap thermal energy radiating away. Hence, during certain operations some body parts should remain covered while others remain exposed, with no extra, unnecessary material interfering with the procedure.

SUMMARY OF THE INVENTION

The instant invention discloses a shaped heating or cooling pad having a particular application when used in the medical field. The shaped pad follows the general contours of the human anatomy. Such shaped pads can be formed in many sizes, ranging from infant to adult, to optimize application of thermal radiation to a particular patient. The pad would be capable of accomodating the following classic positions: Frowlers, e.g. sitting up; prone, e.g. face-down; supine, e.g. on back; Trandelenberg, e.g. body flat and head slightly down; semi-Frowlers, e.g. slightly sitting up; lateral, e.g. on side; and reverse-Trandelenberg, e.g. body flat and head slightly up.

The pad will evenly distribute heat or cold as needed across the length of the body. To achieve this, various thermal radiation means might be used. The preferred embodiment utilizes a chemical reaction pouch for the generation of heat or cold. For instance, a chemical reaction pouch placed inside a surrounding pack can be used wherein the pouch is broken to initiate the thermal generating reaction. Alternatively, a catalyst such a metal disk could be flexed to thereby activate the chemical reaction inside the pad. While the reaction would be effective for only a fixed number of hours, the pad could then be thrown away due to its relatively inexpensive cost. Such disposable pads are beneficial when used with medical operations due to sanitary concerns and problems with sterilizing a reusable pad.

The instant invention alternatively discloses a heating or cooling pad which is inflated with a circulated, thermally controlled fluid, and which takes on a cup-like, concave contour to cradle the patient's body and appendages onto the pad. The plastic pad has a series of parallel channels whereby the pressurized, thermally controlled fluid is injected into an input port and then follows interlaced channels to eventually exit through an outlet port. The pad might also be divided internally to provide separate input and output ports for different sections of the pad. This type of pad might also be constructed of inexpensive, disposable materials.

The relative stiffness of the pad, as formed or inflated, could be used to aid in immobilization of the patient. Accordingly, the pad might incorporate the additional attachment a stiffening material to the back of the pad, such as plastic or cardboard.

The disclosed human shaped heating or cooling pad, regardless of the internal thermal mechanism used, has a series of attachment strips across its bottom side for attachment of modularized segments of insulated material. While a hook and pile attachment, such as that sold under the trademark VELCRO, is particularly well suited for the attachment strips due to its releasability, other materials might be also used. The modular sections are thereby attached with corresponding hook and pile strips. Such modular sections might include, for example, two separate sections for use across each of the legs, two sections across the torso or mid-section, a separate section for use across each arm, and a separate section which attaches to the arm/shoulder area and folds downwards across the left and right portions of the chest. Each of these sections includes an additional hook and pile attachment strip at its free end for securing the insulated material around the patient lying on the pad. This attachment strip could vary in area to accomodate wrapping around and securing different sized appendages of different sized patients.

A separate, optional section of insulated material is provided which can be secured over the torso area, or mid-section, of the patient. This additional section has hook and pile attachment strips around its periphery which can be secured at various points to the pad. The section is segmented into four partitions, attached commonly at the center, where each segment can be individually folded back as necessary to uncover only a small section of the torso or mid-section. A separate headpiece is also disclosed which could be shaped to fit the contours of the patient's head, with the headpiece attaching to the back of the pad with another hook and pile strip. Alternatively, a flat section might be used, with hook and pile around its periphery, which could be folded and fixed into a desired shape around the patient's head, and secured to the heating or cooling pad.

As an alternative to the modularized sections, a one piece section of insulated material might be used which lies underneath and attaches to the heating or cooling pad. The one piece section would have flaps extending outward with attachment strips at the free ends. As similar to the modularized sections, the flaps would wrap around and insulate various body parts as needed. This one piece section might be used with either heating or cooling pad configuration, as well as the optional torso and headpieces.

Thus, an objective of the instant invention is to provide a heating or cooling pad with a plurality of thermally insulated sections which can be modularly attached as needed to thermally influence various body parts and secure them to the pad.

A related objective of the present invention is to provide a heating or cooling pad with modular sections which can be releasably attached and detached to the pad, with one convenient attachment method including hook and pile hook and pile strips.

Another object of the present invention is to provide a heating or cooling pad with a one piece section of insulated material which can be releasably attached to the bottom of the pad and which has flaps of material which extend around the patient.

It is still another related objective of the present invention to provide a heating or cooling pad which is specially shaped to fit the contours of a human shape, with sizes ranging from infant to adult.

It is yet another related objective of the present invention to provide a human shaped heating or cooling pad utilizing a chemical reaction pack capable of generating thermal energy over a sustained period of time.

It is a further objective of the present invention to provide a human shaped heating or cooling pad which inflates via injection of pressurized, thermally controlled fluid and circulates the fluid through interlaced channels running throughout the pad.

It is a related objective of the present invention to provide an inflatable pad, with individualized fluid flow compartments, for more localized control of thermal energy flow through the pad.

It is still a related objective of the present invention to provide the heating or cooling pad above which inflates to form a cup-shaped concave upper surface to cradle the patient's body onto the pad.

It is yet another objective of the present invention to provide a stiffening means for the pad to aid in the immobilization of a patient strapped to the pad.

It is another objective of the present invention to provide a separate compartmentalized section of thermally insulated material which can be releasably attached over the torso area or mid-section of the patient, with individual sections folded back and secured as needed.

It is yet a further objective of the present invention to provide a separate thermally insulated headpiece which can be releasably attached around the patient's head, and to the heating or cooling pad.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

Figure 1A:
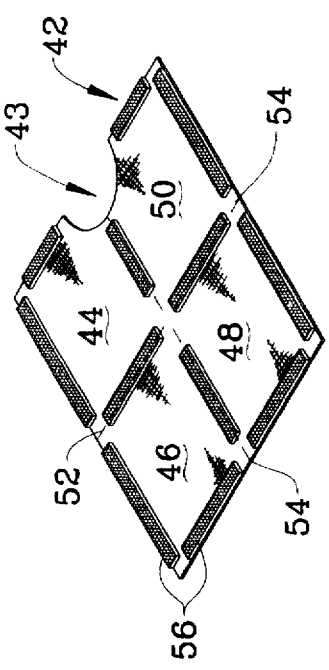
FIG. 1A is a perspective view of two headpieces used to surround and insulate a patient's head.
Figure 1B:
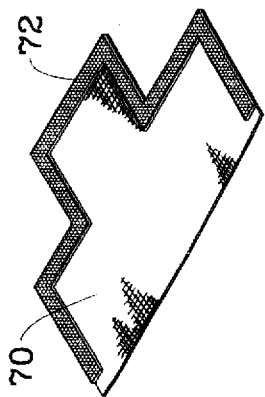
FIG. 1B is a perspective view of an optional, compartmentalized section of insulated material which is releasably attachable over the mid-section of a patient.
Figure 1:
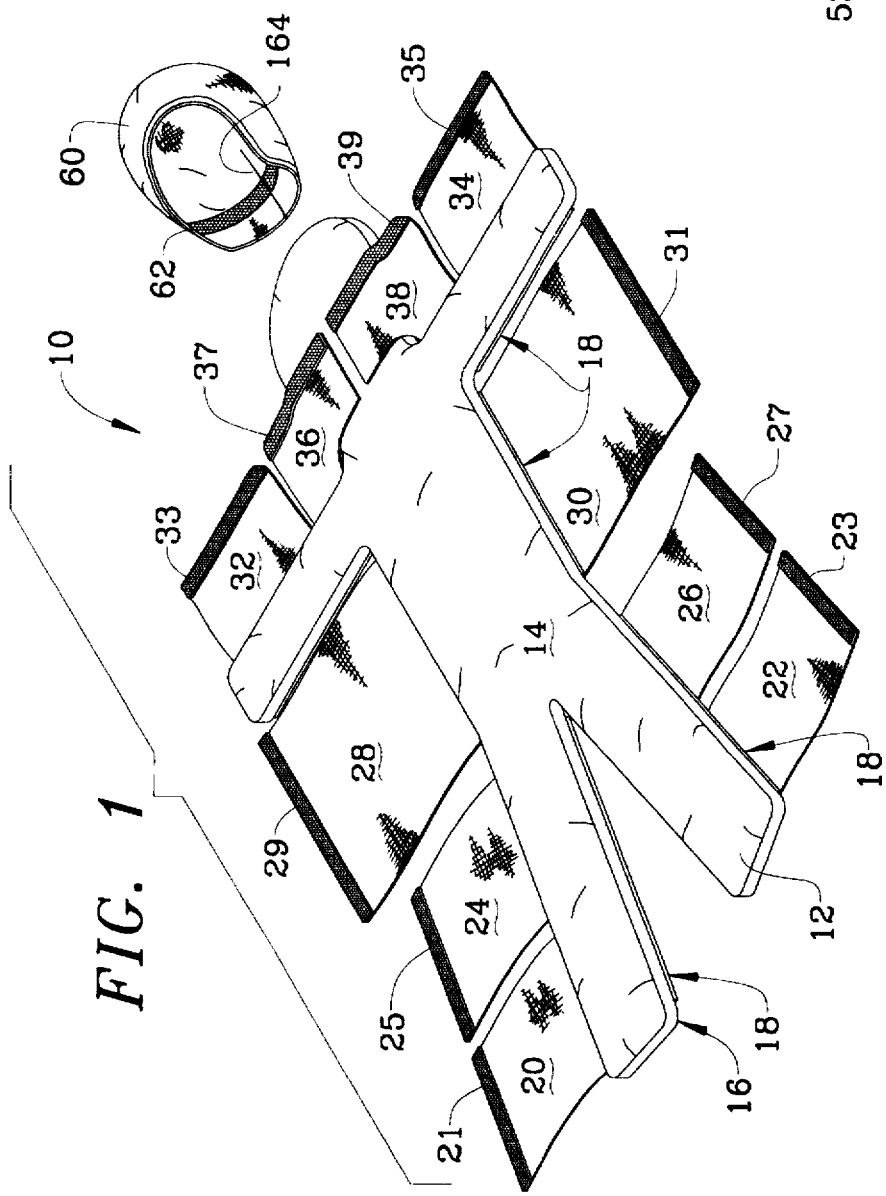
FIG. 1 shows a perspective view of the human shaped heating or cooling pad with modularized sections of thermally insulated material of the instant invention.

Referring now to FIG. 1, a heating or cooling pad device 10 is shown with modular segments of releasably attachable insulated material. The pad 12 is human shaped and formed to lie underneath the patent so as to conform to the shape of the prone or supine body with outstretched arms and legs. Of course, other positions could be accomodated on a pad of this general shape. The pad 12 has an upper surface 14 and a lower surface 16. In the preferred embodiment, the heating or cooling pad 12 is formed from a chemical pack which can generate heat or cold upon activation according to the prior art. Such chemical packs include a pouch suspended within the pack which can be broken to mix the separated chemicals and thereby provide a heating or cooling reaction. Alternatively, a catalyst such as a metal disc might be flexed to initiate the thermal energy releasing reaction. This chemical reaction can evenly supply heat or cold over the upper surface 14 of the pad 12, which will then radiate upward to warm the patient lying on the pad (not shown).

The lower surface 16 has a series of attachment strips 18, wherein hook and pile is ideally suited for this purpose. These attachment strips run along the outer perimeter of the pad 12 with downward facing receiving surfaces. A plurality of modularized, thermally insulated sections of material, shown as 22–38, each have a corresponding attachment strip with an upward facing attachment surface. Such insulated material might consist of products marketed under the trademarks THINSULATE, GORE-TEX, neoprene, or other suitable materials. As shown in this embodiment, these sections include left and right lower leg sections 20 and 22, left and right upper leg sections 24 and 26, left and right torso sections 28 and 30, left and right arm sections 32 and 34, and left and right chest sections 36 and 38.

Each insulated section 20–38 includes a hook and pile attachment strip 21–39 at the free end of the material. This strip might varying in its overall area to provide adjustability for attachment of the material, thereby accomodating different sized appendages on different sized patients. As the section is wrapped around the particular body part of the patient, the attachment strip 21–39 might be attached to the corresponding receiving surface 18 underneath the pad. As shown, the leg sections 20–26 and the arm sections 32–34 would be long enough wrap around the appendage and be secured underneath. Such securement would optimize the trapping and radiating back of heat or cold from the patient's body and from the pad. Securement of the limbs might also aid in performing the surgical procedure or operation, particularly with infants who do not respond well to verbal requests.

The torso sections 28–30 might be formed wide enough so that only one section needs to be used and can be wrapped around the patient's body and secured underneath on the other side. Alternatively, as shown, two sections can be used which then secure to each other in the middle via paired hook and pile strips, or would wrap over each other to provide double insulation. Each chest section 36–38 folds downward from the shoulder portion of the arm and across the left and right chest areas of the patient. The attachment strips 37–39 on the chest sections would attach to corresponding receiving strips (not shown) on the underside of the torso sections 28–30.

FIG. 1A shows alternative versions of insulated materials that can be used to cover the patients head and thereby further conserve thermal energy. The preferred embodiment uses a shaped bonnet 60 which includes an attachment strip 62 for attaching the bonnet 60 to the heating or cooling pad 12. The bonnet 60 also has a slit 64 up the back to permit it to be wrapped around the patient's head, as needed. An alternative embodiment 70 uses a T-shaped piece of insulated material with attachment strips 72 around its periphery. The material 72 can be placed under the pad and/or the patient's head and shaped into a bonnet-like structure via the attachment strips 72.

Referring now to FIG. 1B, an optional section of insulated material 42, with a neck cutout section 43, is shown which might be used over the mid-section of the patient. This section 42 includes four partitioned quadrants 44, 46, 48, and 50, as formed by cuts 52 running perpendicularly from the center of the section 42. Each quadrant can be releasably joined to next quadrant through attachment strips 54 located along the cuts 52. Attachment strips 56 extend around the periphery of each quadrant and can be used to attach section 42 to the heating or cooling pad 12. The benefit of this construction is that the quadrants 44–50 can be individually folded back, and re-attached, in a non-interfering manner to thereby expose only a part of the underlying torso of the patient. When section 42 is used alone, or in conjunction with sections 28–30, maximum conservation of thermal energy can be achieved in the patient, and yet still allow accessibility to particularized parts of the patient.

Figure 2:
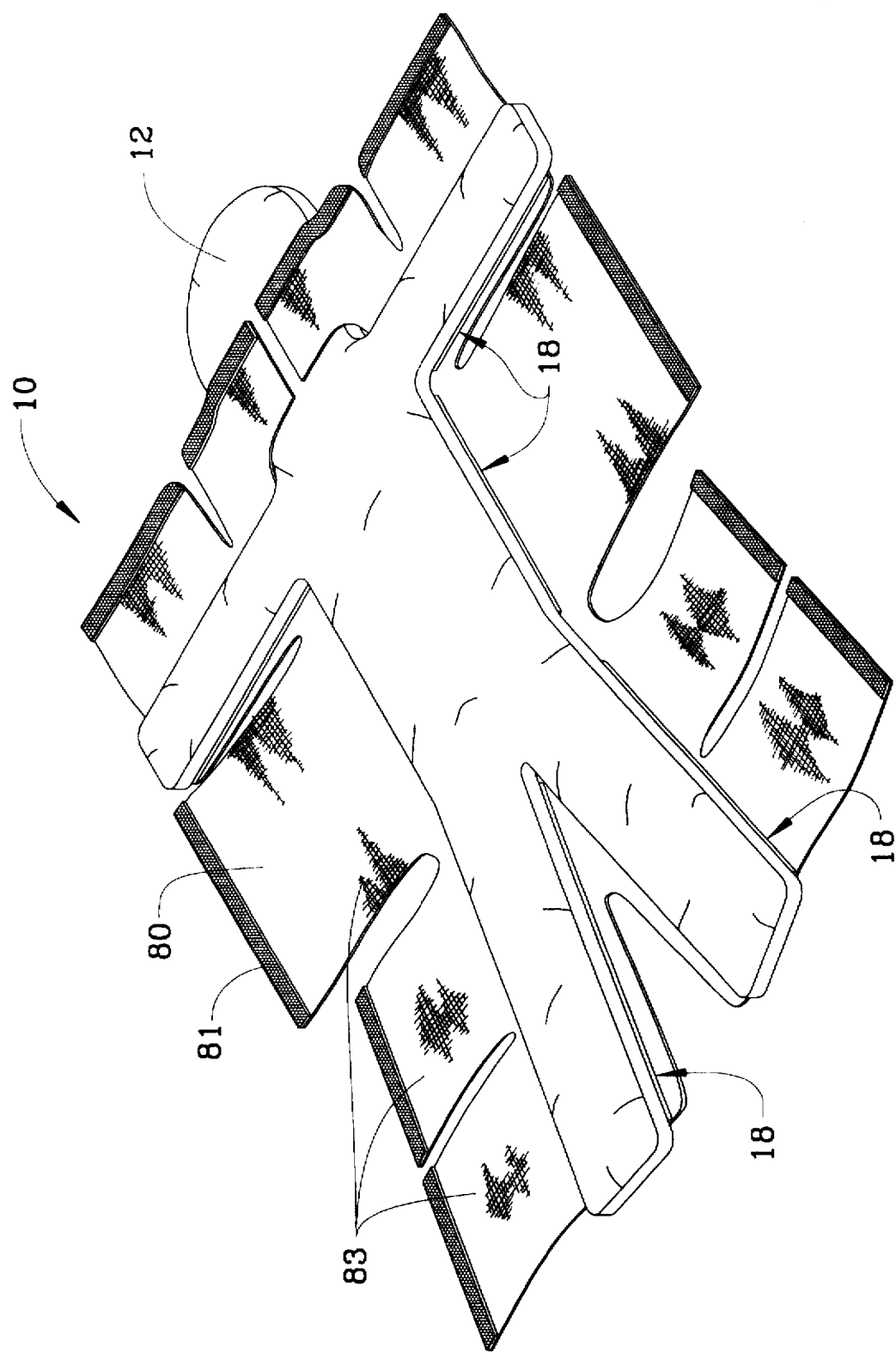
FIG. 2 shows a heating or cooling pad similar to FIG. 1, but with a one-piece section of insulated material which attaches to the bottom of the pad and has flaps which fold around and over the patient.

Referring now to FIG. 2, an alternative embodiment of the heating or cooling pad device 10 is shown wherein a single sheet of insulated material 80 is used underneath the pad 12. Instead of modularized sections being attached to provide material to wrap around and secure the patient, flaps 83 of similarly shaped material extend out from the single sheet 80. The single sheet 80 is secured to the bottom of the pad 12 via attachment strips 18 running along the bottom periphery of the pad 12. As with the modular sections, each flap 83 has a hook and pile attachment strip 81 at its free end for securing the flaps around the patient. While not shown, the optional torso-covering section 42 and the headpiece sections 60, 70 could also be used with the one piece sheet of insulating material 80.

Overall, the modularized insulation sections 20–38, as shown in FIG. 1, provide the most versatility when configuring and using the heating or cooling pad device 10. As such, individualized insulating sections can be applied and/ or detached according to the needs and preference of the doctor or operating personnel. When certain sections are not needed, they will not be attached and can thereby not serve to interfere with the procedure. Accordingly, the pad can be customized by attaching some insulation sections and not attaching others. The pad might even be used alone, with no insulating sections attached.

With the single piece insulation section 80 of FIG. 2, the pad might be setup and configured more quickly. For instance, the single piece section 80 needs only to be laid flat, with the pad 12 attached thereon to the appropriate attachment strips. Each insulating flap, however, is present in this configuration, whether it is ultimately used or not. Some users might find this extra material to be a distraction which does not warrant the easier setup. Hence, the modularity of the primary embodiment presents a ready solution and allows custom configuration with only the desired sections attached to the pad.

Figure 3:
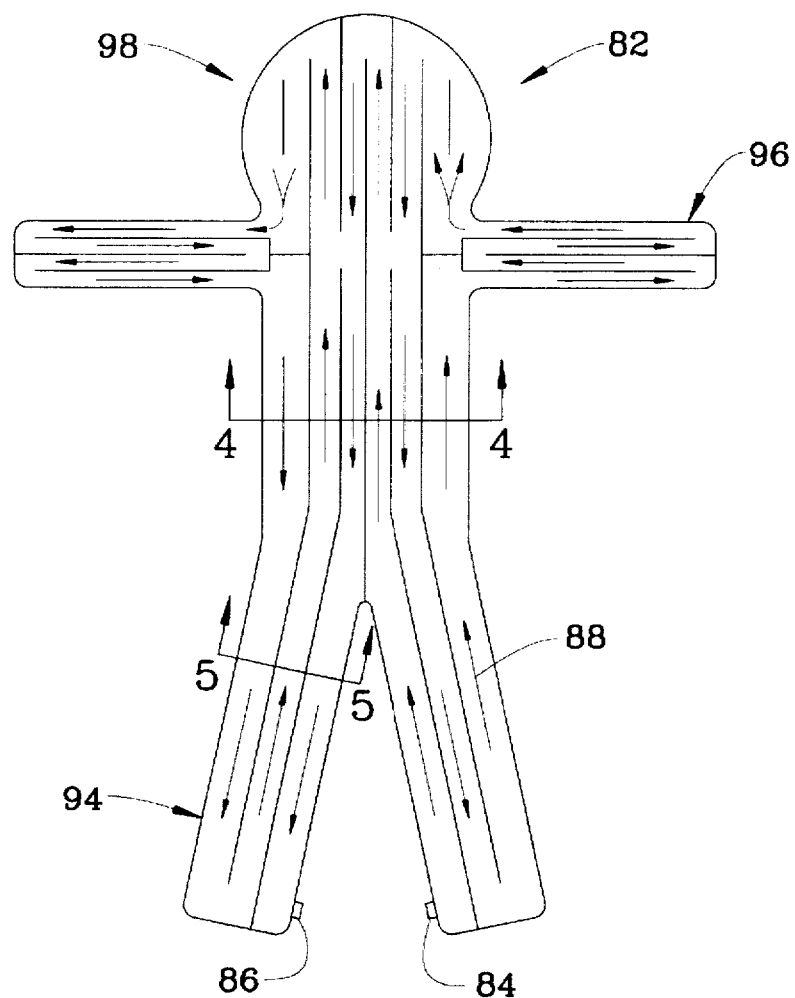
FIG. 3 shows a front, pictorial view of an inflatable, human-shaped heating or cooling pad with arrows showing the flow pattern of thermally controlled fluid running through the interlaced channels.
Figure 4:
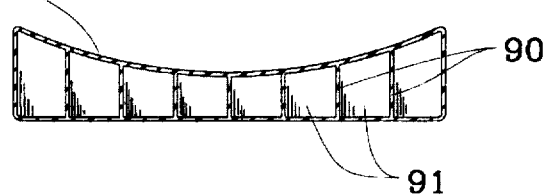
FIG. 4 shows a cross-sectional view along cut 4—4 of FIG. 3 wherein the contour of the inflated pad surface along the torso is shown.
Figure 5:
FIG. 5 shows a cross-sectional view along cut 5—5 of FIG. 3 wherein the contour of the inflated pad surface along the leg is shown.

Referring now to FIG. 3, an alternative heating or cooling pad 82 is shown which has a series of parallel, interlaced channels running throughout the pad. An inlet port 84 is connected to a pressurized source (not shown) which supplies heated or cooled fluid, typically water or saline, to the pad. In response to the pressure, the pad inflates as the fluid circulates up and down the interlaced channels as generally shown by the arrow pattern 88. The circulated fluid eventually exits through outlet port 86. Referring also to FIG. 4, a cross-sectional view of the heating or cooling pad 82 along cut 4—4 of FIG. 3 is shown. This figure illustrates the channel structure which makes up the inflatable pad. As shown, various walls 90 separate each channel 91 to properly direct the fluid throughout the pad 82. The upper surface 92 is formed to take on a curved shape when the pad is fully inflated so as to cradle the patient on the pad. FIG. 5 shows a cross-sectional view of the pad 82 along cut 5—5 of FIG. 3. This figure shows the related curvature formed along the surface 92 of the leg portions 94 of the pad. Such curvature also exists along the arm portions 96 and head portion 98 of the pad. The relative amount of curvature, as well as the firmness of the pad, can be controlled to some extent by varying the pressurization of the fluid entering and exiting the pad.

Figure 3A:
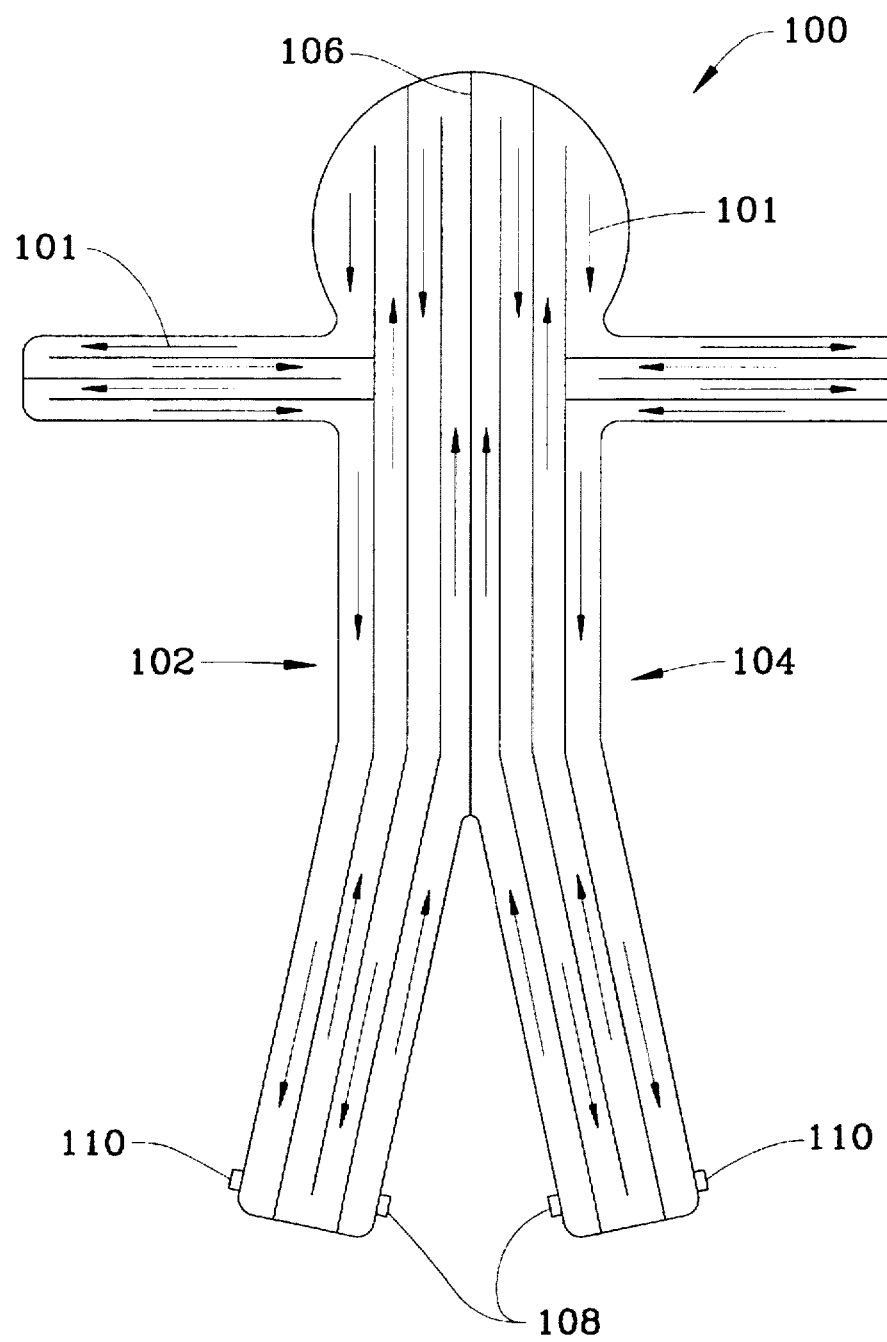
FIG. 3A shows an alternative pictorial view of the inflatable pad wherein the left and right sides are separately inflated, with separate inlet and outlet ports for circulating the pressurized fluid.

Referring also to FIG. 3A, yet another alternative heating or cooling pad 100 is shown with channels for directing the flow pattern 101 of the pressurized thermally controlled fluid. In this embodiment, the left side 102 and right side 104 of the pad 100 are separated by a central barrier 106. As a result, both the left and right sides 102, 104 can be independently controlled via separate inlet 108 and outlet ports 110. This would allow a user to apply more or less heat or cold to each side as needed for a particular operation.

As with the chemical reaction heating or cooling pads 12 of FIGS. 1 and 2, the pressurized heating or cooling pads 82 and 100 would have hook and pile attachment strips along the periphery of the bottom for attachment of insulated sections of material. Also as before, these sections could be modularly attached as needed to provide versatility in setting up the pad. Alternatively, a single piece section of insulated material 80 could be used with flaps that fold around the pad. The insulated material accessories 43, 60, and 70 could similarly be used to conserve thermal energy around the mid-section and head areas of the patient. While not shown, even more control over heating or cooling of the pad could be achieved by providing a larger number of separately channeled sections with separate inlet and outlet ports to service each section.

Either pad might be reusable; e.g. certain forms of chemical packs can be regenerated to produce heat or cold again upon activation, and the fluid pressurized pad need only be reconnected to a thermally controlled fluid source. Such pads could be cleaned and sterilized via conventional means. However, such pads could also be constructed of low cost, yet durable, materials which would provide the desired option of disposability. With medical operations involving blood and/or other bodily fluids, such disposability would be particularly desirable.

While not shown, a stiffening means such a plastic or cardboard could readily be attached to the back of the pad 16 to provide increased rigidity. Such stiffening means might consist of pad shaped cutouts, or more simply, longitudinal strips which could be adhered to the pad. Such stiffening means would aid in operations or procedures where the patient, or portions of the patient, needed to be immobilized. When strapped to the stiffened pad, the increased resistance would prevent the patient from moving.

It is to be understood that while a certain forms of the invention are illustrated, they are not to be limited to the specific forms or arrangements of parts herein described and shown. It will be apparent to those skilled in the art that various changes may be made without departing from the scope of the invention and the invention is not to be considered limited to what is shown in the drawings and descriptions.

What is claimed is:

1. A patient body temperature regulation device for use in surgical operations and medical procedures comprising:

a pad having an upper and lower surface, said pad shaped to conform to a human form;

means for generating and evenly distributing thermal energy throughout said pad;

a plurality of insulated material sections individually releasible attached to the periphery of said pad;

attachment means for securing said pad in a fixed position;

wherein the patient lies upon said pad and thermal energy radiates upwards to be trapped by said insulated sections which securely wrap around and insulate various body parts of a patient.

2. The patient body temperature regulation device according to claim 1, wherein said pad is sized to accommodate an infant up to an adult.

3. The patient body temperature regulation device according to claim 1, wherein said means for generating thermal energy is defined as a chemical reaction pouch forming said pad.

4. The patient body temperature regulation device according to claim 1, wherein a stiffening means is adhered to said lower surface of said pad.

5. The patient body temperature regulation device according to claim 1, wherein said pad includes hook and pile fastener attachment strips along a bottom periphery for receivable interfacing with corresponding hook and pile fastener attachment strips on each said insulated material section.

6. The patient body temperature regulation device according to claim 5, wherein said insulated material sections have hook and pile attachment strips for securing said wrapped around portion to hook and pile attachment strips on said pad.

7. The patient body temperature regulation device according to claim 1, wherein said insulated material sections include left and right lower leg sections, left and right upper leg sections, left and right torso sections, left and right arm sections, and left and right chest sections, wherein each section can be releasably attached as needed.

8. The patient body temperature regulation device according to claim 7, wherein said insulated material further includes a headpiece means with an attachment strip for releasably securing said headpiece around the patient's head and to said pad.

9. The patient body temperature regulation device according to claim 7, wherein said insulated material further includes a separate torso section for placement over the mid-section of the patient, said section having releasable attachment strips around its periphery, and separable quadrants formed by perpendicular cuts extending from the perimeter of the torso section towards its center, said cuts being releasably closable via attachment strips along said cuts, wherein said torso section can be secured over the patient's mid-section and said quadrant material can be individually folded and secured back as needed.

10. The patient body temperature regulation device according to claim 1, wherein said thermal energy generation means includes a pad with at least one fluid inlet and corresponding fluid outlet port, said pad having interacting fluid conducting channels which direct pressurized heated fluid from each said inlet port through said pad to said corresponding outlet port.

11. The patient body temperature regulation device according to claim 10, wherein said pad inflates due to the introduction of said pressurized fluid to form a curved concave upper surface which cradles the patient lying on said pad.

12. The patient body temperature regulation device according to claim 10, wherein said pad is separated internally into a left and right section, each said section having a fluid inlet and corresponding fluid outlet port, each said pad section having interlaced fluid conducting channels which direct pressurized thermally controlled fluid from each said inlet port through said pad to said corresponding outlet port.

13. The patient body temperature regulation device according to claim 1, wherein said conforming, human shaped pad is used without any insulated material sections so attached to the periphery of said pad.

14. A patient body temperature regulation device for use in medical operations and medical procedures comprising:

a pad having an upper and lower surface, said pad shaped to conform to a human form;

means for generating and evenly distributing thermal energy throughout said pad;

a single piece insulated material section attached with a releasible attachment means to the lower side of the pad, said section having a plurality of insulation material flaps which extend around said pad;

attachment means for securing said pad in a fixed position;

wherein the patient lies upon said pad and thermal energy radiates upwards to be trapped by said flap sections which wrap around and various body parts of a patient and are secured with further attachment means.

15. The patient body temperature regulation device according to claim 14, wherein said releasable attachment means includes hook and pile fastener attachment strips.

16. The patient body temperature regulation device according to claim 14, wherein said pad is sized to accommodate an infant up to an adult.

17. The patient body temperature regulation device according to claim 14, wherein said means for generating thermal energy is defined as a chemical reaction pouch forming said pad.

18. The patient body temperature regulation device according to claim 14, wherein said thermal energy generation means includes a pad with at least one fluid inlet and corresponding fluid outlet port, said pad having interacting fluid conducting channels which direct pressurized thermally controlled fluid from each said inlet port through said pad to said corresponding outlet port.

19. The patient body temperature regulation device according to claim 18, wherein said pad inflates due to the introduction said pressurized fluid to form a curved concave upper surface which cradles the patient lying on said pad.

20. The patient body temperature regulation device according to claim 14, wherein a stiffening means is adhered to said lower surface of said pad.

* * * * *